United States Patent [19]

Alchas

[11] Patent Number: 5,030,210
[45] Date of Patent: Jul. 9, 1991

[54] CATHETER VALVE ASSEMBLY

[75] Inventor: Paul G. Alchas, Wayne, N.J.

[73] Assignee: Becton, Dickinson and Company, Franklin Lakes, N.J.

[21] Appl. No.: 153,685

[22] Filed: Feb. 8, 1988

[51] Int. Cl.⁵ .......................................... A61M 25/00
[52] U.S. Cl. ...................................... 604/247; 604/9
[58] Field of Search .................... 604/247, 9, 280; 137/853, 493

[56] References Cited

U.S. PATENT DOCUMENTS

| | | |
|---|---|---|
| 1,719,428 | 7/1929 | Friedman . |
| 2,616,429 | 11/1952 | Merenlender . |
| 3,111,125 | 11/1963 | Schulte . |
| 3,525,357 | 8/1970 | Koreski et al. ............... 604/247 X |
| 3,799,172 | 3/1974 | Szpur . |
| 4,549,879 | 10/1985 | Groshong et al. . |
| 4,559,046 | 12/1985 | Groshong et al. . |
| 4,657,536 | 4/1987 | Dorman ........................ 604/247 |
| 4,685,905 | 8/1987 | Jeanneret nee Aab . |
| 4,701,166 | 10/1987 | Groshong et al. . |
| 4,953,640 | 6/1988 | Nichols et al. ................ 604/247 |

FOREIGN PATENT DOCUMENTS 727959  4/1955  United Kingdom ............... 604/247

Primary Examiner—Stephen C. Pellegrino
Attorney, Agent, or Firm—Robert P. Grindle

[57] ABSTRACT

An improved valve assembly is provided for the distal end of a catheter, and particularly a central venous catheter for controlling fluid passage from the catheter to the blood flow passage in which it is inserted, and flow in the opposite direction. A relatively thin sheath wall covers the distal fluid opening of the catheter, and includes a slit for responding rapidly to pressure differentials on either side of the slit opening to allow fluid passage, as required. In addition, the distal end of the catheter, and the side walls thereof adjacent the end, are covered by a thin sheath which serves to impart a small degree of thickness or "body" to the end of the catheter except at the opening thereof. More importantly, with the arrangement here the integrity of the catheter wall is far less compromised.

8 Claims, 2 Drawing Sheets

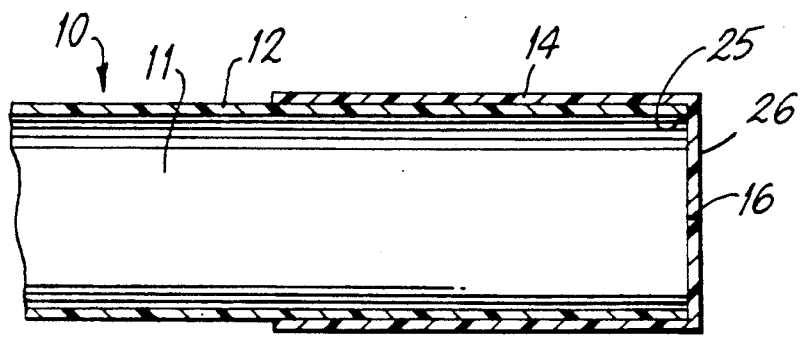
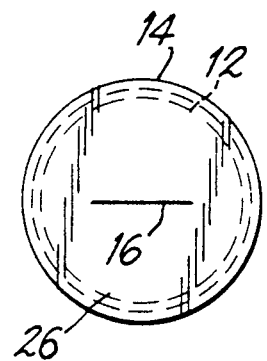
FIG. 1   FIG. 2
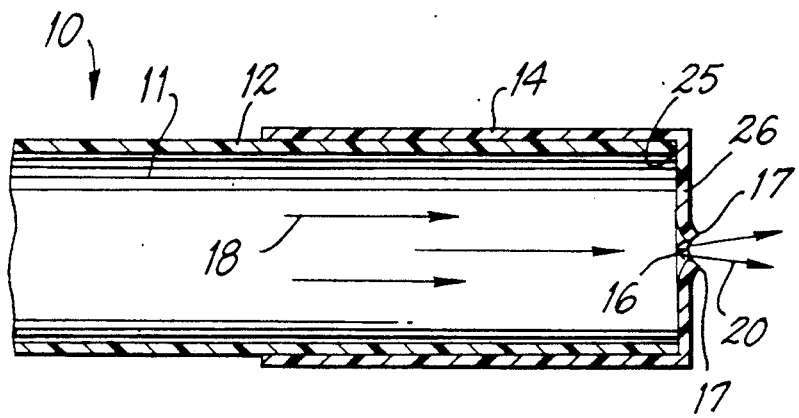
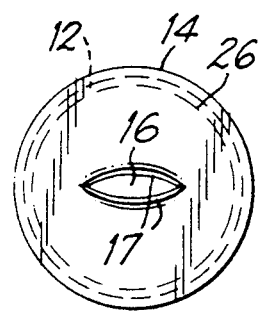
FIG. 3   FIG. 4
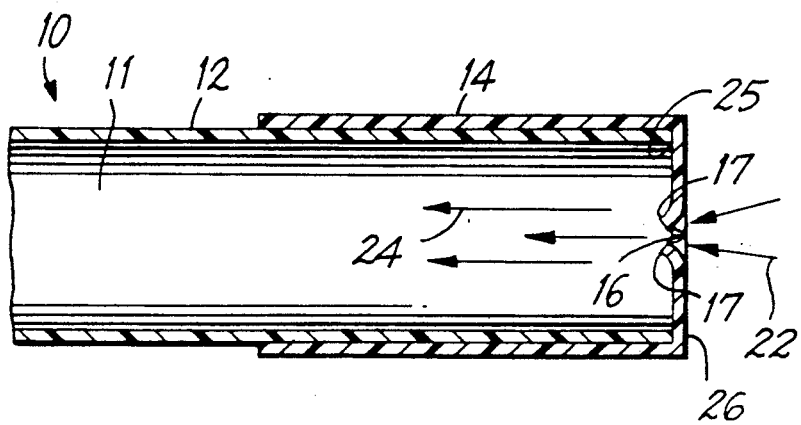
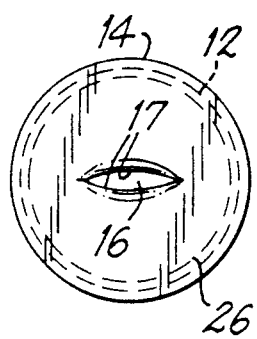
FIG. 5   FIG. 6

CATHETER VALVE ASSEMBLY

BACKGROUND AND DESCRIPTION OF THE INVENTION

The present invention relates generally to catheter assemblies, and more particularly to a catheter having a fluid control valve in the distal end thereof for controlling delivery of fluids from the catheter to the blood flow passage in which it is inserted, and vice versa.

Various procedures for intravenous therapy, including hyperalimentation and the administration of chemotherapeutic drugs, require the use of a catheter which remains in the patient's body for a period of days, weeks, or even months. In a typical procedure, the catheter is inserted through the subclavian vein, located near the collar bone and advanced to the superior vena cava, an area of substantial blood flow to the heart. In some long term catheterization procedures, the physician reroutes the exposed end of the catheter from the original entry, near the collar bone, subcutaneously through the patient's body and out into the abdominal area so that the patient can resume normal activities without having a catheter protruding from the collar bone area.

Such catheterization procedures have been performed routinely with a conventional catheter having an open distal end. By the term "distal" is meant the leading edge of the catheter upon insertion into the body. Blood flow out of the body is prevented by occluding a portion of the catheter which is external to the patient's body, such as by covering the portion of the catheter outside the body by an injection cap which includes a pierceable septum for allowing injection and withdrawal of fluids.

This form of catheter has certain disadvantages in that the open end of the catheter, which is positioned in the patient's body, provides an area for the formation of blood clots. The potential for formation of clots is undesirable because clots occlude the catheter and prevent its use. Furthermore, a clot can separate from the catheter and travel to other areas of the vascular system and cause injury by occluding another blood vessel. The open distal end type of catheter must be flushed frequently with a heparinized saline solution to clean the catheter area and reduce the potential for clot formation.

This periodic maintenance provides a potential for irritation and infection by manipulation of the catheter and introduces an anticoagulant into the blood stream which may affect the patient or any blood test results from specimens taken from the patient. In addition, the external cap may be removed inadvertently which creates the danger of introducing an air embolus into a vein and injuring the patient. Furthermore, the blunt open end of the catheter interferes with blood flow and is believed to increase the occurrence of turbulent eddies which eddies may also promote clot formation.

Such problems are avoided if the central venous catheter is provided with a closed distal end with a port or valve arrangement. U.S. Pat. No. 3,111,125 teaches a shunt apparatus with an outlet tube having a closed distal end and a plurality of slits around the periphery of the distal end of the tube acting as slit valves. Fluid pressure in the tube forces the slits open so that fluid flows freely when a sufficient pressure differential exists between the fluid within the tube, and the area outside the tube. Along these lines, U.S. Pat. Nos. 4,559,046 and 4,701,166 teach a catheter device for intravenous therapy having a flexible closed distal end including a slit-type valve as described above with, in addition, a twisted wire removable stiffener which is used to facilitate insertion of the catheter into a patient and then removed, leaving the catheter in place.

A valve is desirable in a central venous catheter for controlling fluid flow through the catheter and into the patient, as described above and further to allow fluid flow from the patient's vascular system out of the catheter when obtaining, for example, a blood sample. Slit valves of past structures present problems because inwardly directed pressure tends to shut the slit valve more tightly rather than to open it. U.S. Pat. Nos. 4,559,046 and 4,701,166, as discussed above, teach the use of soft materials such as silicone rubber to overcome this problem which silicone rubber is made in a thin cross-section and treated with dimethylsiloxane for lubrication of the slit edges and for weakening, and making the catheter wall more pliable, in order to facilitate the two-way valve function.

However, this form of slit-type valve works well only where outward flow is desirable and inward flow is not desirable because of its directional properties. Because the distal end of the catheter is made of softer material and further treated to be weaker in order to attempt to overcome deficiencies of a pressure activated slit valve, the tip of the catheter becomes weaker.

This weakened tip is more prone to bending caused by patient movement or muscular movement within the patient's body and the tip may be bent in such a manner as to open the valve in the absence of fluid pressure differential across the valve. A weakened tip will also be more prone to collapse during aspiration. Also, silicone lubrication can wear off making it difficult to open the valve during aspiration. There is a trade-off, therefore, between optimizing the valve performance so that the valve is responsive to fluid pressure differentials, and providing a valve that stays shut when required and is strong enough not to collapse during aspiration.

There is still a need for a reliable, easily fabricated catheter having a closed distal end and a valve which will minimize the potential for damage to cellular elements in liquid passing through the valve, which can be used successfully for aspiration without collapsing, while at the same time minimizing the potential for inadvertent opening of the valve. Such inadvertent opening can result in patient blood loss or the introduction of an air embolus into the patient's vascular system or formation of a clot in the lumen.

One such arrangement is taught in co-pending application Ser. No. 881,148, filed Jul. 2, 1986 now U.S. Pat. No. 4,737,152, issued Apr. 12, 1988 wherein the fluid control valve has a cylindrical side wall describing a lumen therethrough, a proximal end and a closed distal end, and includes a slit through the side wall positioned adjacent the distal end with the slit angularly oriented with respect to the longitudinal axis of the catheter.

The slit is defined by two opposed faces formed in the side wall. The catheter housing includes a conduit wherein the proximal end of the catheter is connected to the housing so that the conduit and lumen are in fluid communication. A stylet is positioned within the lumen. A valve control knob includes a passageway therethrough, and is rotatably connected to the housing so that the passageway and the conduit are in fluid communication. The knob engages the stylet causing rotation of the stylet, which in turn causes rotation of the closed distal end of the catheter causing the opposed faces of the slit to separate, forming an opening for allowing fluid communication between the lumen and the exterior of the catheter.

This arrangement has the advantage that the operator is allowed to selectively open and shut the valve regardless of pressure differentials. However, this arrangement is more complicated in that it includes considerably more structure in order to open and close the valve.

With this invention, by contrast, a valve arrangement is provided in the form of a slit valve which responds to pressure differentials on either side of the valve, without causing the catheter to collapse. Moreover, the arrangement is such that the forward end of the catheter includes a closed distal end which is comprised of sufficient body that it will not bend or become occluded because of body movements of the patient, muscular movements of the patient or aspiration vacuum. Moreover, the valve in the form of a slit, in accordance with this invention, is provided in a comparatively thin wall covering the distal opening of the catheter, so that it responds rapidly to pressure differentials on either side thereof. Because of this, the valve opens readily to the presence of medication being fed into the catheter for introduction into the blood supply of the patient. By the same token, the valve opens in response to the opposite pressure differential for obtaining a blood sample from the patient, as required.

This is achieved by selecting a conventional catheter with an open distal end and providing a sheath covering over that open distal end. In this way, the structural integrity of the catheter wall is not altered. The sheath has the effect of forming a dual wall structure over the end of the catheter adjacent the distal end thereof while providing a single thin wall in the area of the slit valve. Because of this, the thin wall in which the valve of the invention is positioned responds much more rapidly than would be the case if the valve were positioned in the conventional thicker wall of the catheter body itself. Nevertheless, with the dual wall structure in the areas other than where the valve is positioned, the catheter distal end has more "body" for sustaining less damage and/or injury from patient movement, readjustment of the positioning of the valve of the invention or aspiration vacuum. More importantly, there is less involvement in the structural integrity of the catheter wall than is the case when a slit is positioned in the catheter wall itself.

In considering generally the conditions for forming the catheter valve assembly of the invention, preferably the catheter is comprised of polyurethane having a thickness within the range of 10 and 30 mils. Positioned over the open distal end of the catheter is a sheath comprised, preferably, of the same material as the catheter i.e., polyurethane. The sheath wall is of a thickness within the range of 2 and 10 mils. It should be understood that the sheath may be comprised of a material different from the catheter wall itself. Other materials for forming either or both of the catheter and the sheath may include, for example, silicone rubber, polyvinylchloride, polyethylene or polytetrafluoroethylene.

As discussed above, the slit forming the valve of the invention is positioned in the sheath in the area where the sheath does not cover a portion of the wall of the catheter itself, such as the immediate distal end thereof. As a result, the thickness of the wall surrounding the slit valve of the invention will be within the range of 2 and 10 mils which causes the slit valve to respond much more rapidly to pressure differentials on either side thereof. Nevertheless, the adjacent wall of the catheter itself surrounding the valve wall will have a thickness within the range of 12 and 40 mils, thus providing more body for the catheter adjacent to the valve.

As a result, because the distal end of the catheter is not open, blood reflux in the catheter lumen is eliminated thereby eliminating the potential for clot formation, and occlusion of the catheter. As a result of this, routine flushing of the catheter lumen is not necessary. Moreover, because there is a valve covering the open end of the catheter, introduction of air embolus into the vasculature is eliminated, should the injection cap on the proximal end of the catheter outside the body be removed or fall off.

Of course, turbulent eddies are reduced around the open end of the lumen of the catheter since it is not open and is protected by the thin wall of the sheath of the invention carrying the slit valve. Because of this, potential clot formation on the exterior wall of the catheter is reduced. Finally, because the material adjacent the valve is not treated to weaken it (because it is not necessary) there is much less chance of failure.

As further illustrative of the invention herein, the sheath may be within the range of between about 5 and 20 millimeters in length. The slit valve may be of a length within the range of between about 30 and 70 percent of the inner diameter of the catheter.

Other objects and advantages of this invention will be apparent from the following description, the accompanying drawings, and the appended claims.

DESCRIPTION OF THE DRAWINGS

FIG. 1 is a partial longitudinal sectional view of the distal end of a catheter assembly illustrating the invention;

FIG. 2 is an end plan view showing the right-hand end of the catheter assembly of FIG. 1;

FIG. 3 is a partial longitudinal sectional view of the catheter assembly of FIG. 1 showing the valve arrangement of the invention open for dispensing fluid from the catheter into the vein of a patient;

FIG. 4 is an end plan view of the right-hand end of the catheter assembly of FIG. 3;

FIG. 5 is a partial longitudinal sectional view of the catheter assembly of FIG. 1 showing the valve thereof in the position wherein the catheter assembly is obtaining a blood sample of a patient, for example;

FIG. 6 is an end plan view of the right-hand end of the catheter assembly of FIG. 5;

DETAILED DESCRIPTION OF THE INVENTION

Figure 7:
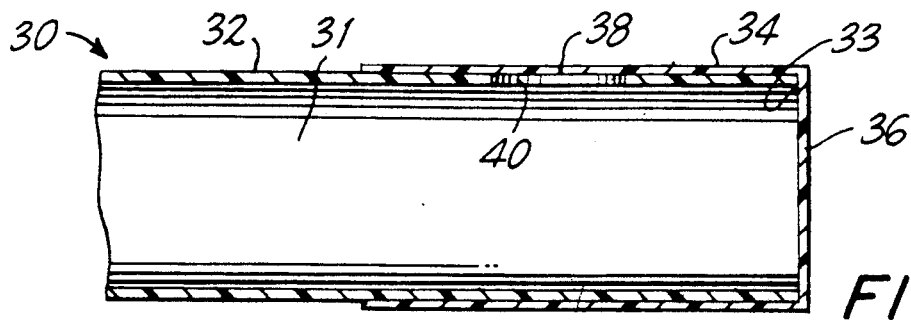
FIG. 7 is a partial longitudinal sectional view of a valve assembly for the distal end of a catheter illustrating a further embodiment of the invention herein.
Figure 8:
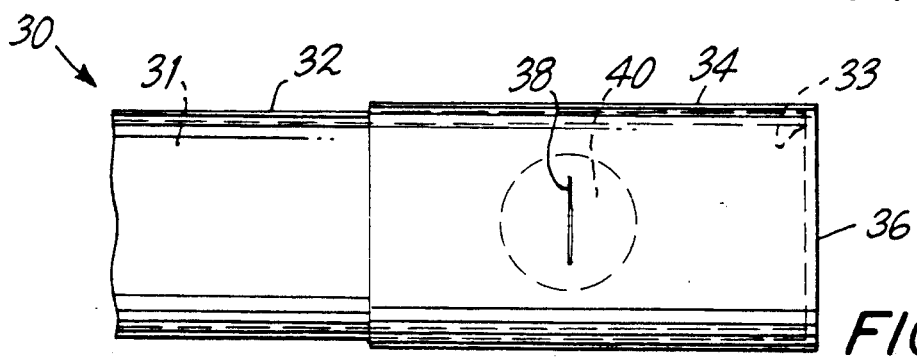
FIG. 8 is a top plan view of the catheter assembly of FIG. 7.
Figure 9:
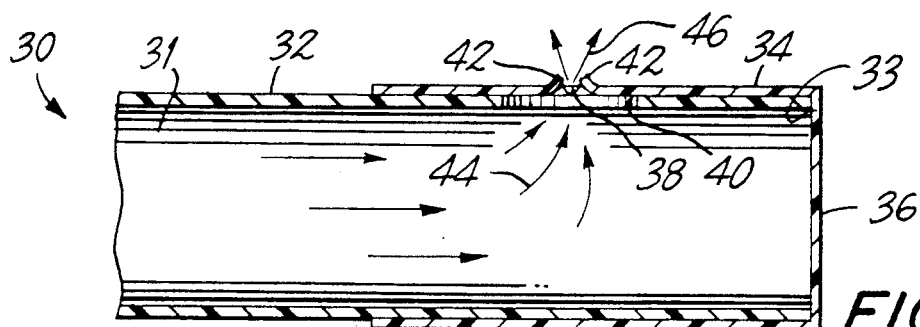
FIG. 9 is a partial longitudinal sectional view of the assembly of FIG. 7 showing the slit valve of the invention in its open position.
Figure 10:
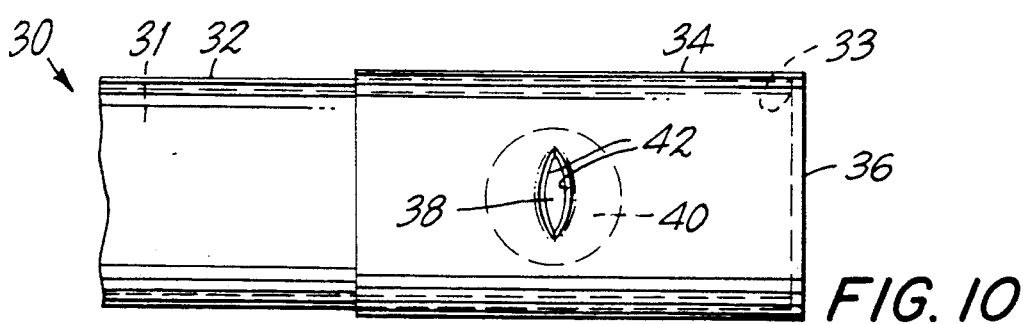
FIG. 10 is a top plan view of the assembly of FIG. 9.

Referring to the drawings in which like reference characters refer to like parts throughout the several views thereof, FIG. 1 shows one embodiment of catheter assembly 10 of the invention which shows the open distal end 25 of the catheter 12. As will be understood by practitioners-in-the-art, catheter 12 is an elongated tube extending from an open proximal end to distal end 25, only a part of which tube is shown in the Figures. Catheter 12 is shown as having a single lumen 11, but it will be understood that two or more lumens may be included. Positioned over the open distal end 25 of catheter 12 is a sheath 14, having an end wall 26 for covering the open end 25 of catheter 12. Positioned centrally of wall 26 of sheath 14 is a slit valve 16. As can be seen in FIG. 2, the valve 16 extends a substantial distance across the circular end wall 26 of sheath 14.

As is clearly shown in the Figures, sheath 14 is dimensioned so that the internal hollow cavity formed by the walls of the sheath 14 grip the outer surfaces of catheter 12 in an interference fit so as to maintain the sheath positioned as shown on the distal end 25 of catheter 12. Alternatively, sheath 14 may be heat bonded to the surface of catheter 12, or the surfaces may be joined by adhesives.

Referring now to FIG. 3, arrows 18 show the flow of a medication being fed through catheter assembly 10 to be introduced into the vein of a patient in which the assembly 10 has been inserted. Because of the increased pressure internally of catheter 12, valve 16 is open so that the cooperating adjacent walls or flaps 17 thereof provide a passage for the flow of medication through the slit valve 16 in the direction of arrows 20. Thus, FIGS. 3 and 4 show the position of slit valve 16 for an infusion procedure of the arrangement of the invention herein.

Referring now to FIG. 5, in the use of the invention herein for aspiration through a slit valve 16 of the invention, the valve 16 is shown in its position for aspiration purposes. Thus, in instances wherein the physician requires the obtaining of a blood sample through the assembly of the invention which has been inserted into a patient, the catheter assembly 10 is shown in the position for such taking in FIG. 5. That is, arrows 22, 24 indicate the passage of fluid through open valve 16 with the flaps 17 thereof opening internally of the catheter assembly 10. As can be seen from this arrangement, valve 16 is immediately responsive to pressure differentials on either side thereof because of the relative thin wall 26 of sheath 14 covering the open distal end 25 of catheter 12.

Referring now to FIGS. 7-10, inclusive, a further embodiment of the invention is shown. In this arrangement, a partial sectional view of the distal end of catheter 32 is shown with lumen 31, and with the assembly 30 thereof including a sheath 38 covering the open distal end 33 with an end wall 36 of sheath 34. In this case, however, a separate opening 40 is positioned in the annular wall of catheter 32. Positioned in sheath 34, in the opening 40 of catheter 32 is a slit valve 38. Thus, except for end wall 36, the valve assembly 30 includes a dual wall construction similar to the embodiment shown in FIG. 1 for providing greater "body" to the distal end of catheter assembly 30. This has the effect, as discussed above, of preventing damage and/or distortion to the distal end of catheter 32 so that there is no occluding of the passage of fluids in either direction through catheter 32 for the administration of medication therethrough in one direction, or for obtaining a blood sample in the opposite direction.

At any rate, with this arrangement, as with the arrangement shown in FIG. 1, slit valve 38 responds rapidly to pressure differential, because of the comparatively thin wall of sheath 34, for causing the flow of fluid in the direction of arrows 44, 46 causing flaps 42 of valve 38 to open for the passage of fluid therethrough, in the infusion position of the assembly of the invention. Of course, it will be understood that valve 38 operates in the opposite direction for the taking of the blood sample, in the same manner as the arrangement shown in FIG. 1.

Figure 11:
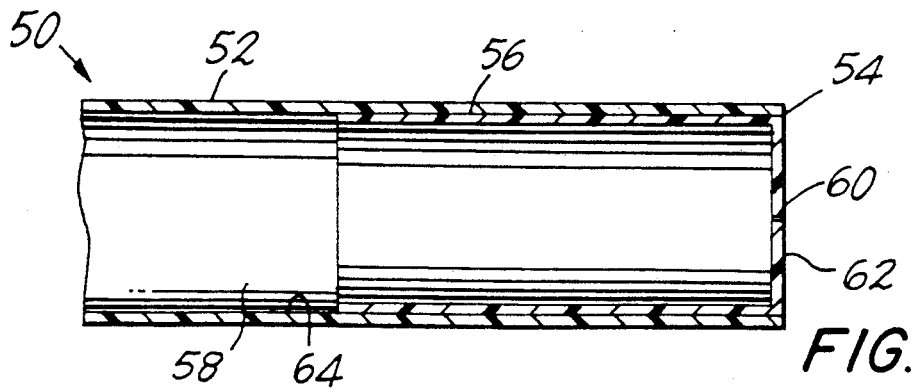
FIG. 11 is a partial longitudinal sectional view of a valve assembly for the distal end of a catheter illustrating an additional embodiment of the invention.

In the embodiment in FIG. 11, an assembly generally designated 50 is shown with a portion of the distal end of catheter 52 having a distal opening 54 closed by a sheath 56 of the invention. In this embodiment, sheath 56 is inserted into opening 54 so that the outer surfaces of sheath 56 engage the internal walls 64 of catheter 52. In this embodiment as with the others, valve 60 is located in the sheath wall 62 so as not to interfere with the integrity of the walls of catheter 52.

Thus, as will be appreciated from the above, there is provided in accordance with this invention, an improved valve assembly for the distal end of a central venous catheter, for example, which valve assembly provides a substantial increase in the stability of the distal end of the catheter upon insertion into a patient. Nevertheless, the structure includes a simplified slit valve which responds rapidly to pressure differentials on opposite sides thereof. Even so, the construction herein is a simplified arrangement requiring no special housings or devices for manipulating the opening and closing of the valve.

While the forms of apparatus herein described constitute preferred embodiments of the invention, it is to be understood that the invention is not limited to these precise forms of apparatus, and that changes may be made therein without departing from the scope of the invention which is defined in the appended claims. For example, while the orientation of the slit valves shown in the end wall of the sleeve covering the distal end of the catheter is shown to be perpendicular to the longitudinal axis of the catheter, it should be understood that the slit may be oriented at various angles to the position shown.

What is claimed is:

1. A catheter assembly for controlling positively the passage of fluids therethrough to and from the fluid flow passage in which it is inserted, characterized by
   (a) an elongated catheter tubular body having a sidewall;
   (b) said catheter tubular body having an open proximal end, an open distal end and an opening in the sidewall spaced from the distal end;
   (c) one or more lumens extending in said catheter tubular body from said open proximal end to said open distal end;
   (d) a substantially tubular sheath positioned over the said open distal end of said tubular body, and extending from said open distal end to a point spaced from said open distal end;
   (e) a substantial portion of one surface of said sheath engaging one surface of said catheter tubular body;
   (f) said sheath engaging said catheter tubular body in a non-slip engagement;

(g) a three position two-way slit valve positioned in said sheath; and (h) said three position two-way slit valve positioned in the wall of said sheath adjacent the catheter sidewall opening.

2. The assembly of claim 1, further characterized by (a) said catheter tubular body is a member selected from the group consisting of polyurethane, silicone rubber, polyvinyl chloride, polyethylene and polytetrafluoroethylene.

3. The assembly of claim 1, further characterized by (a) said sheath is comprised of a member selected from the group consisting of polyurethane, silicone rubber, polyvinyl chloride, polyethylene and polytetrafluoroethylene.

4. The assembly of claim 1, further characterized by (a) said sheath and said tubular body are both comprised of a member selected from the group consisting of polyurethane, silicone rubber, polyvinyl chloride, polyethylene and polytetrafluoroethylene.

5. The assembly of claim 1, further characterized by (a) the walls forming said elongated tubular body being within the range of between about 10 and 30 mils thick.

6. The assembly of claim 1, further characterized by (a) the walls of said sheath being within the range of between about 2 and 10 mils thick.

7. The assembly of claim 1, further characterized by (a) the said non-slip engagement of the surface of said sheath with the surface of said catheter tubular body being an interference fit.

8. The assembly of claim 1, further characterized by (a) the said non-slip engagement of the internal surface of said sheath with the outer surface of said catheter tubular body being a heat bond.

* * * * *